ASH TREE

Filed July 29, 1969 2 Sheets-Sheet 1

INVENTOR:

RICHARD EUGENE SCHLAPFER

BY Burns, Doane, Benedict, Swecker & Mathis

INVENTOR:
RICHARD EUGENE SCHLAPFER
BY Burns, Doane, Benedict, Swecker & Mathis

United States Patent Office

Plant Pat. 3,088
Patented Mar. 28, 1972

3,088
ASH TREE

Richard Eugene Schlapfer, Arlington, Nebr., assignor to Marshall Nurseries, Arlington, Nebr.

Filed July 29, 1969, Ser. No. 845,920
Int. Cl. A01h *5/12*
U.S. Cl. Plt.—51 1 Claim

ABSTRACT OF THE DISCLOSURE

This invention relates to a new and distinct variety of ash tree which is believed to be related to the species *Fraxinus pennsylvanica* (red ash). In contrast to this known variety the new variety (a) bears no flowers or fruit, (b) has less serrated leaflets which are broader and a darker green, (c) has longer petiolules, (d) has a slower growth habit which produces an ovoid more compact crown, (e) has rounded dark brown buds, (f) has leaf scars which are prominently notched at the upper margin, and (g) has resilient bark which can be depressed by pressure of the finger.

DESCRIPTION OF NEW VARIETY

The present new and distinct variety of ash tree was found as a seedling growing in a cultivated area. More specifically, the new variety was found in a block of seedling green ash (*Fraxinus pennsylvanica lanceolata*) growing at Arlington, Nebr., on property of the assignee. Seed for the planting of the block of seedlings was obtained from green ash trees growing within the general vicinity of Arlington, Nebr. No attempt was made to prevent other seed from blowing into the area where the seedlings were grown. The pollen parent of the new variety is unknown. The new and distinct variety of ash tree has been named the Emerald ash.

Because of the obvious distinctive characteristics of the new variety the plant was segregated and asexually reproduced by me the next season by budding onto green ash understock. As confirmed by a plurality of asexual reproductions, the distinguishing characteristics of the variety come true to form and are established and transmitted through succeeding propagations. The asexual reproductions were conducted at Arlington, Nebr., on property of the assignee hereof.

The new variety has developed to maturity (i.e. approximately 15 years of age) and is believed to be sterile. No flowers or fruit have formed. Accordingly the litter of winged fruit commonly present on the ground surrounding ash trees is avoided as are volunteer seedlings which make the new variety particularly suited for planting as a street, lawn, and shade tree.

The new variety is characterized by a slower growth habit than the related red ash, green ash, and Marshall's seedless green ash (*Fraxinus pennsylvanica lanceolata:* Marshall). Such slower growth habit results in a highly attractive planting having a very uniform, compact and dense ovoid crown. The new variety attains a height of approximately forty feet.

Unlike the green ash and Marshall's seedless green ash the leaves including leaflets, petiolules and petioles of the new variety are prominently pubescent.

Figure 1:
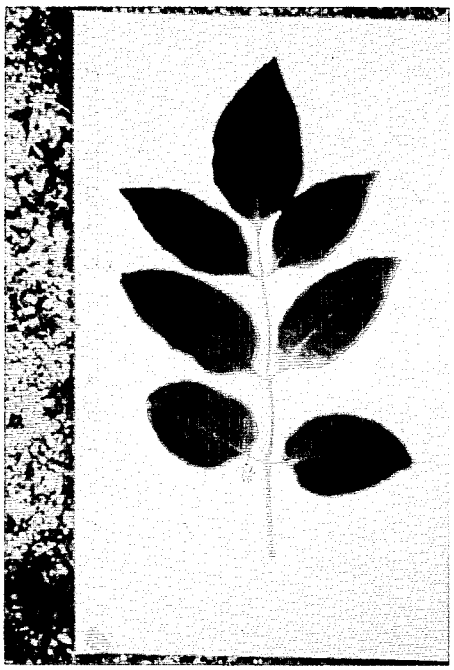
FIG. 1 shows the upper surface of a representative leaf of the new variety.
Figure 2:
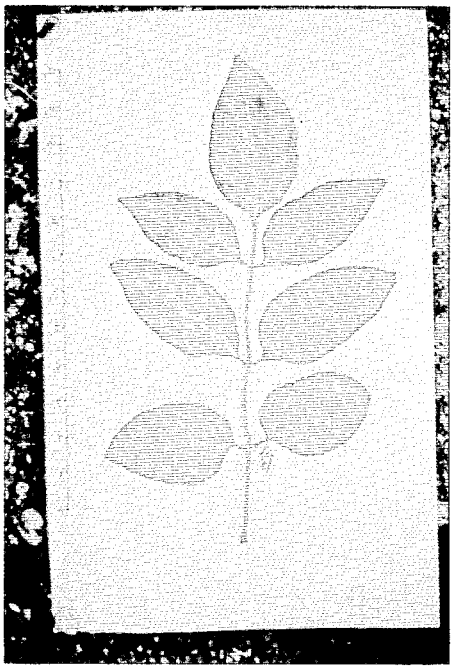
FIG. 2 shows the beneath surface of the same leaf shown in FIG. 1.

The leaflets of the new variety possess a distinctive configuration when compared with the leaflets of the red ash, green ash, and Marshall's seedless green ash. More specifically, the leaflets of the new variety are broader, i.e. more elliptic and less lanceolate, as shown in FIGS. 1 and 2. The narrow acute apex which is characteristic of the leaflets of these known varieties is commonly substantially more blunt in the new variety. The upper surface of the leaflets of the new variety are a substantially deeper green than the leaflets of the red ash and green ash. As shown in FIGS. 1 and 2 the beneath surface of the leaflets of the new variety is a lighter green than the upper surface. The leaflets of the new variety are either smooth or sparingly serrated at relatively wide intervals in contrast to the generally more serrated leaflets of the red ash, green ash, and Marshall's seedless green ash.

The petiolules which bear the leaflets of the new variety are longer than those commonly observed upon the red ash, green ash, and Marshall's seedless green ash.

Figure 3:
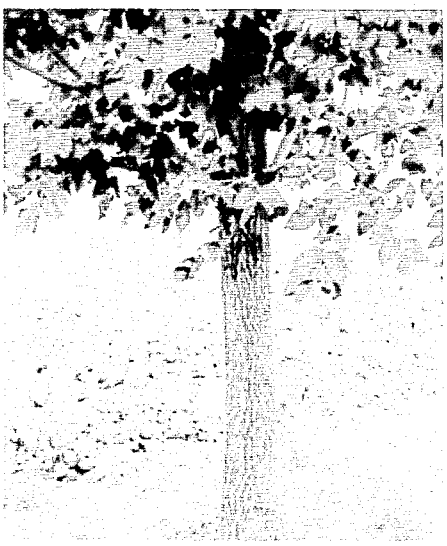
FIG. 3 shows the trunk portion of the new variety.
Figure 4:
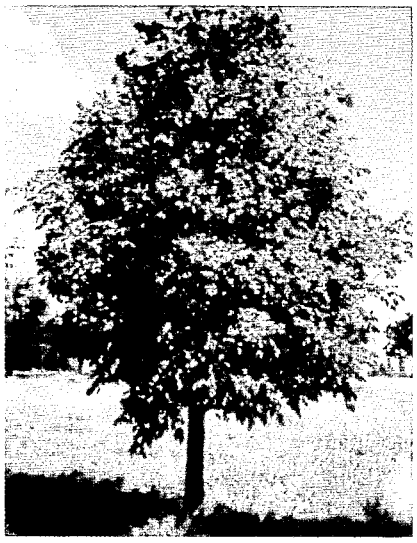
FIG. 4 shows the compact configuration assumed by the foliage of the new variety.

As shown in FIG. 3, the bark of the new variety is interlaced and deeply furrowed, not unlike the red ash. Such characteristics are apparent from youth. The bark of the new variety is resilient and can be depressed by pressure of the finger, unlike the firm and rigid bark structure of related ashes. When released after being depressed, the bark will assume essentially its original configuration. No borer, drought, or disease damage to the new variety has been observed.

Figure 5:
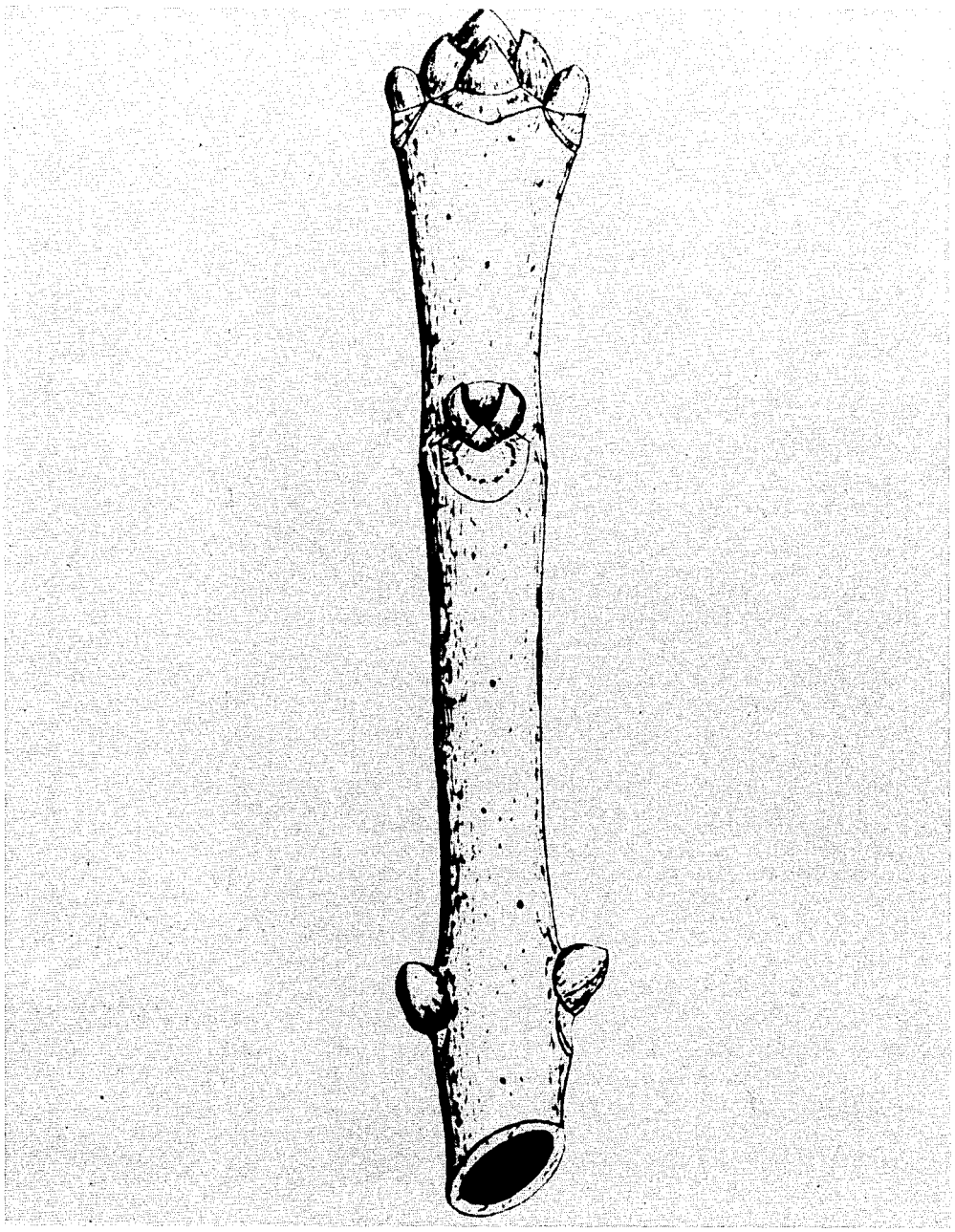
FIG. 5 shows a winter twig of the new variety.

The buds of the new variety are rounded, dark brown, and opposite. As indicated in FIG. 5, the terminal bud of the new variety is substantially larger than the lateral buds. The buds are born upon strout grey pubescent twigs. The leaf scar is prominently notched at its upper margin contrary to that commonly exhibited by the red ash, green ash, and Marshall's seedless green ash.

The leaves of the new variety change to yellow in the fall and are retained approximately three weeks longer than the leaves of other ash trees growing in the immediate vicinity, i.e. green ash, and Marshall's seedless green ash.

The following is a detailed description of my new variety with color terms being utilized to convey their ordinary dictionary meaning:

Parentage: A seedling of an unknown variety believed to be related to the species botanically known as *Fraxinus pennsylvanica.*

Propagation: Holds its distinguishing characteristics through succeeding propagations by budding.

Locality where grown and observed: Arlington, Nebr.

Tree: Upright; small to medium size (approximately 40 feet maximum height); relatively slow growth habit; stiff ascending branches; very uniform, compact and dense ovoid crown.

*Bark.*—Interlaced and deeply furrowed from youth; resilient.

*Twigs.*—Strong (not willowy), and pubescent (current season's growth). Terminal buds—dark brown and rounded. Lateral buds—substantially smaller than terminal buds.. Leaf scars—prominently notched at upper margin. Color—grey.

Foliage:

*Leaves.*—Opposite; pinnately compound of normally 7 leaflets; from 10 to 15 inches long; pubescent.

*Leaflets.*—Length—from 3 to 5 inches. Width—from 1.5 to 3 inches across widest portion. Shape—ovate to oblong-lanceolate. More rounded and less acute at the apex than red ash, green ash, and Marshall's seedless green ash. Margin—smooth or sparingly serrated at relatively wide intervals. Color—dark green above (FIG. 1). Paler green beneath (FIG. 2). Leaflets change to pale yellow in fall and remain on tree approximately three weeks longer than green ash and Marshall's seedless green ash growing in same locality.

*Petiolules.*—Long, normally 0.3 to 0.7 inches long, and pubescent.

*Flowers or fruit.*—None observed even on mature tree (i.e. approximately 15 years of age).

I claim:

1. A new and distinct variety of *Fraxinus pennsylvanica* ash tree, substantially as shown and described, characterized particularly by (a) absence of flowers or fruit, (b) smooth or sparingly serrated leaflets having a dark green upper surface, (c) long petiolules, (d) slow growth habit which produces an ovoid compact crown, (e) rounded dark brown buds, (f) leaf scars which are prominently notched at the upper margin, and (g) resilient bark which can be depressed by pressure of the finger.

No references cited.

ROBERT E. BAGWILL, Primary Examiner